United States Patent [19]

Kuhlmann et al.

[11] Patent Number: 5,182,247
[45] Date of Patent: Jan. 26, 1993

[54] SULFATED CATALYST FOR SKELETAL ISOMERIZATION OF OLEFINS

[75] Inventors: Erven J. Kuhlmann, Hopewell Junction; James R. Pascoe, Fishkill; James E. Browne, Beacon; Kevin J. Martin, Wappingers Falls, all of N.Y.

[73] Assignee: Texaco Inc., White Plains, N.Y.

[21] Appl. No.: 653,217

[22] Filed: Feb. 11, 1991

[51] Int. Cl.$^5$ ............................................. B01J 27/053
[52] U.S. Cl. ...................................... 502/217; 585/671
[58] Field of Search ........................ 502/217; 585/671

[56] References Cited

U.S. PATENT DOCUMENTS

| 3,268,609 | 8/1966 | Nixon | 585/671 X |
| 4,722,986 | 2/1988 | Young | 502/168 X |
| 5,036,035 | 7/1991 | Baba et al. | 502/217 X |

FOREIGN PATENT DOCUMENTS

| 2371961 | 7/1978 | France | 502/217 |
| 1030242 | 5/1966 | United Kingdom | 585/671 |

*Primary Examiner*—W. J. Shine
*Attorney, Agent, or Firm*—Robert A. Kulason; James J. O'Loughlin; Vincent A. Mallare

[57] ABSTRACT

Normal olefins such as n-butene can be converted to branched species by skeletal isomerization over catalysts containing solid acids prepared by sulfating catalyst precursors containing hydrous metal oxides—e.g., aluminas, silica-aluminas or clays treated with sulfuric acid, metal sulfates, sulfur trioxide or organic sulfates. The catalyst precursors are sulfated sufficiently to produce the desired skeletal isomerization without substantial cracking under suitable isomerization conditions.

1 Claim, 3 Drawing Sheets

SULFATED CATALYST FOR SKELETAL ISOMERIZATION OF OLEFINS

BACKGROUND OF THE INVENTION

1. Field of the Invention

The present invention relates to a process for the preparation of isoalkenes by catalytic conversion of n-alkenes, catalysts which are suitable for this conversion, and a process for the preparation of such catalysts.

This invention further relates to olefin isomerization.

In one of its more specific aspects, this invention relates to selective isomerization.

2. Information Disclosure Statement

Isomerization processes can be directed towards either skeletal isomerization or double bond isomerization. Skeletal isomerization is concerned with reorientation of the molecular structure in respect to the formation or elimination of side chains. Double bond isomerization is concerned with relocation of the double bond between carbon atoms while maintaining the backbone of the carbon structure. Most isomerization processes give rise only to double bond isomerization.

It is frequently necessary to convert olefins into other olefins having a different skeletal arrangement. For example, normal butenes are converted into isobutene for polymerization, alkylation, disproportionation, etc. Similarly, normal amylenes must be converted to isoamylenes prior to dehydrogenation to isoprene.

While a number of catalytic materials possess some activity for such a conversion, not all possess sufficient selectivity to be economical. Because the feeds are generally the relatively reactive olefins, many catalysts cause undesirable side reactions such as polymerization or cracking. Moreover, some catalysts are difficult to prepare and regenerate. Additionally, some catalysts are less effective with certain olefins than with others. Consequently, there is a continuing interest in the development of new skeletal isomerization catalysts and processes to improve efficiencies and to give optimum results for various industrial requirements. A comprehensive review is provided by V.R. Choudhary in "Catalytic Isomerization of n-butene to Isobutene," *Chem. Ind. Dev*, pp. 32–41 (1974).

It is generally known that n-paraffins with, for example, 4 to 7 carbon atoms can be converted to the corresponding isomeric paraffins by using suitable acid catalysts in the temperature range of from 100° to 250° C. Examples of this process are the numerous isomerization processes used in the petrochemical and mineral oil industries for increasing the octane number of light, paraffinic mineral oil fractions. Furthermore, it is known that, in contrast to this, olefins of the same number of carbon atoms cannot be converted to the corresponding iso-olefins or can only be converted to the corresponding iso-olefins under difficult conditions, for example at very high temperatures and with poor yield. The attempts hitherto described in the literature for the direct isomerization of the skeleton of e.g. n-butene to give isobutene or e.g. of n-pentene to give isopentenes over catalysts arranged in a fixed bed are characterized by only initially high yields and selectivities, which diminish and deteriorate considerably after a short period of operation, often after only a few hours. The deterioration in the yields and selectivities is generally attributed to the loss of actively effective catalyst surface or to the loss of active centers. In addition to this, high catalyst fouling rates, formation of oligomers and cracking reactions are observed.

Thus, in U.S. Pat. No. 3,531,542, a process is described for obtaining isobutene from n-butene, in which an $Al_2O_3$ catalyst arranged in a fixed bed is employed in a number of stages. In U.S. Pat. No. 3,663,453 the same conversion is conducted also in a fixed bed, with a catalyst consisting of zirconium oxide and an $Al_2O_3/ZrOCl_2$ catalyst. The catalytic isomerization of olefinic hydrocarbons in a fixed bed is also described in U.S. Pat. No. 2,568,964. It is reported that carbon deposits form on the catalyst material during the isomerization process, which reduce the activity and necessitate periodic regeneration of the catalyst. It is stated that the catalyst regains its full activity after regeneration, but at least one disadvantage which remains is that the isomerization process itself has to be interrupted during the period of regeneration.

As is known, butylene or butene exists in four isomers: butene-1, cis-butene-2, its stereo-isomer trans-butene-2, and isobutene. Conversions between the butenes-2 are known as geometric isomerization, whereas those between butene-1 and the butenes-2 are known variously as position isomerization, double-bond migration, or hydrogen-shift isomerization. The aforementioned three isomers are not branched and are known collectively as normal or n-butenes. Conversion of the n-butenes to isobutene, which is a branched isomer, is widely known as skeletal isomerization. The same general terminology is used when discussing skeletal isomerization of other n-alkanes and olefins, as well as paraffinic compounds such as n-alkenes.

Isobutene has become more and more important recently as one of the main raw materials used in the production of methyl tert-butyl ether (MTBE), an environmentally-approved octane booster to which more and more refiners are turning as metallic additives are phased out of gasoline production. However, processes for the skeletal isomerization of olefins e.g., to produce isobutene, are relatively non-selective, inefficient, and short-lived because of the unsaturated nature of these compounds. On the other hand, positional and skeletal isomerization of paraffins and alkyl aromatics are fairly well established processes, in general utilizing catalysts typically comprising metallic components and acidic components, under substantial hydrogen pressure. Since paraffins and aromatics are stable compounds, these processes are quite successful. The heavier the compounds, in fact, the less severe the operating requirements.

Olefins, however, are relatively unstable compounds. Under hydrogen pressure, they are readily saturated to the paraffinic state. Indeed, three processes could be combined for the conversion of n-alkenes to isoalkenes, for example: first, hydrogenation of olefins into paraffins; second, skeletal isomerization of the paraffins; and third and finally, dehydrogenation of the skeletal paraffins into the desired iso-olefin. In this process combination, the first and third processes are accompanied by large heat effects and therefore may require several stages each; for light hydrocarbons, the conditions for the third process of the combination are usually quite severe.

Furthermore, in the presence of acidity, olefins can polymerize, crack and/or transfer hydrogen. Extensive polymerization would result in poor yields, and short operating cycles. Similarly, cracking would reduce yield. Hydrogen transfer would result in saturated and highly unsaturated compounds, the latter being the common precursors for gum and coke. Any theoretical one step process for producing skeletal isomers of, for example, n-butenes, would have to be concerned with the unwanted production of butanes and the reverse problem of production of butadienes. On top of all of these problems, it is well known that skeletal isomerization becomes more difficult as hydrocarbons get lighter.

Skeletal isomerization of olefins is known to be accomplished by contacting unbranched or lightly branched olefins with acidic catalysts at elevated temperatures. The process is generally applicable to the isomerization of olefins having from 4 to about 20 carbon atoms and is especially applicable to olefins having from 4 to about 10 carbon atoms per molecule. The process may be used to form isobutene from normal butenes, methyl pentenes and dimethyl butenes from normal hexenes, and so forth.

Known skeletal isomerization catalysts include aluminas and halogenated aluminas, particularly F- or Cl-promoted aluminas. Supports employed in such catalysts are either alumina or predominantly alumina due mainly to the high acidity of alumina. See Choudhary, V.R., "Fluorine Promoted Catalysts: Activity and Surface Properties", *Ind. Eng. Chem., Prod. Res. Dev.*, 16(1), pp. 12–22 (1977) and U.S. Pat. No. 4,400,574. See also U.S. Pat Nos. 3,381,052, 4,405,500 and 3,444,096. Numerous catalysts employ a metal or metal oxide in conjunction with a halide-treated metal oxide. For example, U.S. Pat. No. 4,410,753 discloses isomerization catalysts comprising $Bi_2O_3$ on fluorided alumina and U.S. Pat. No. 4,433,191 discloses skeletal isomerization catalysts comprising a Group VIII metal on halided alumina. U.S. Pat. No. 4,548,913 discloses catalysts for the skeletal isomerization of n-alkenes to iso-alkenes, containing admixtures of zeolites and clays which are preferably fluorine-treated.

Many of the catalysts including halide-treated components require periodic addition of halide materials to maintain catalyst activity; for example, see U.S. Pat. Nos. 3,558,734 and 3,730,958. Disadvantages of using such catalysts include the corrosion of process equipment due to the presence of halide ions and the necessity of adding halide materials as part of the feed as the reaction proceeds. Isobutene yields of 17 to 33 weight percent are typically reported when using halided catalysts, based upon a review of various patents cited in this disclosure.

Various techniques have been employed to improve the effectiveness of materials such as alumina and silica as skeletal isomerization catalysts. For example, U.S. Pat. No. 3,558,733 discloses methods for activating alumina catalysts with steam, U.S. Pat. No. 4,405,500 discloses catalysts prepared by controlled deposition of silica on alumina and U.S. Pat. No. 4,587,375 discloses a steam-activated silicalite catalyst. In addition, various metal oxides have been used to improve the effectiveness of catalysts based upon alumina, silica or the like.

U.S. Pat. No. 4,654,463 discloses (in Claim 2) catalysts for the skeletal isomerization of olefins comprising bromided aluminas. Optionally, such alumina-based catalysts can include minor portions of various metal oxides, including, e.g. molybdenum and tungsten oxides. The active alumina and other metal oxides can be combined as physical mixtures or chemically bonded as in alumina-molybdena. Similarly, U.S. Pat. No. 4,778,943 discloses catalysts for the skeletal isomerization of olefins containing halogen-treated alkaline earth compounds, (all highly basic materials) optionally in conjunction with other metal oxides including alumina, molybdenum oxide and tungsten oxide.

The addition of sulfate ion to zirconia, alumina and other metal oxides has been reported to produce an enhancement in catalytic activities for acid-catalyzed reactions. It has been reported that sulfated alumina can isomerize 1-butene to 2-butenes but that no skeletal isomerization could be detected (see W. Przystajko et al in *Applied Catalysis*, Vol. 15, pp. 265–75 (1985). Recently been found to be active in the skeletal isomerization of n-butenes, and the addition of 8 weight percent sulfate to alumina provided a catalyst which produced "significant amounts of the skeletal isomer." However, the activity for isobutene production reportedly decreased by roughly 60 percent during the first ninety minutes of these runs. See J.C. Luy et al in *React. Kinet. Catal. Lett.*, Vol. 36, pp. 275–79 (1988)

An object of this invention is an improved process for the skeletal isomerization of olefins, especially for the isomerization of n-butenes to form isobutene. A more specific object is an easily prepared, stable, active and selective isomerization catalyst and process for skeletal isomerization of olefins. Other objects and advantages of the invention will be apparent from the following description, including the drawing and the appended claims.

SUMMARY OF THE INVENTION

In accordance with the present invention, a catalyst composition for the skeletal isomerization of normal olefins comprises a sulfur oxide or a sulfate species on a hydrous metal oxide support in which the metal is selected from Groups IIIA, IVA, IVB and VIIIB of the Periodic Table.

The catalyst is preferably substantially free of halides, and the hydrous metal oxide support preferably comprises at least one alumina such as gamma alumina.

The catalyst is prepared by a process comprising the steps of:

(a) drying the hydrous metal oxide support to an optimum moisture content;

(b) treating said support with a sulfating agent to form a sulfated catalyst precursor and deposit sufficient sulfate species to catalyze the skeletal isomerization of olefins under isomerizing conditions; and (c) calcining the sulfated precursor to generate a finished catalyst comprising a solid acid.

Further in accordance with the invention, processes for converting normal olefins to branched chain olefins by skeletal isomerization comprise steps of contacting the olefins (which can be at least about 20 weight percent of a mixed feedstock) under skeletal isomerization conditions with a catalyst of the invention. Operable conditions include temperatures in the range of about 300° to 500° C., pressures ranging from about 0.5 to about 40 psig and weight hourly space velocities (WHSV) ranging from about 0.1 to about 320 weight of olefin/weight of catalyst per hour. The normal olefins can have from 4 to about 12 carbon atoms, preferably about 4 to 6, and preferably include n-butenes.

In a preferred embodiment, the normal olefins are contained in a feedstock which also can contain branched olefins, and the product of the skeletal isomerization step is reacted with an alkanol having from 1 to about 5 carbon atoms (such as methanol or ethanol) under catalytic conditions effective to produce at least one methyl tertiary-alkyl ether, such as methyl tertiary-butyl ether or ethyl tertiary-butyl ether.

DETAILED DESCRIPTION OF THE INVENTION

Figure 1:
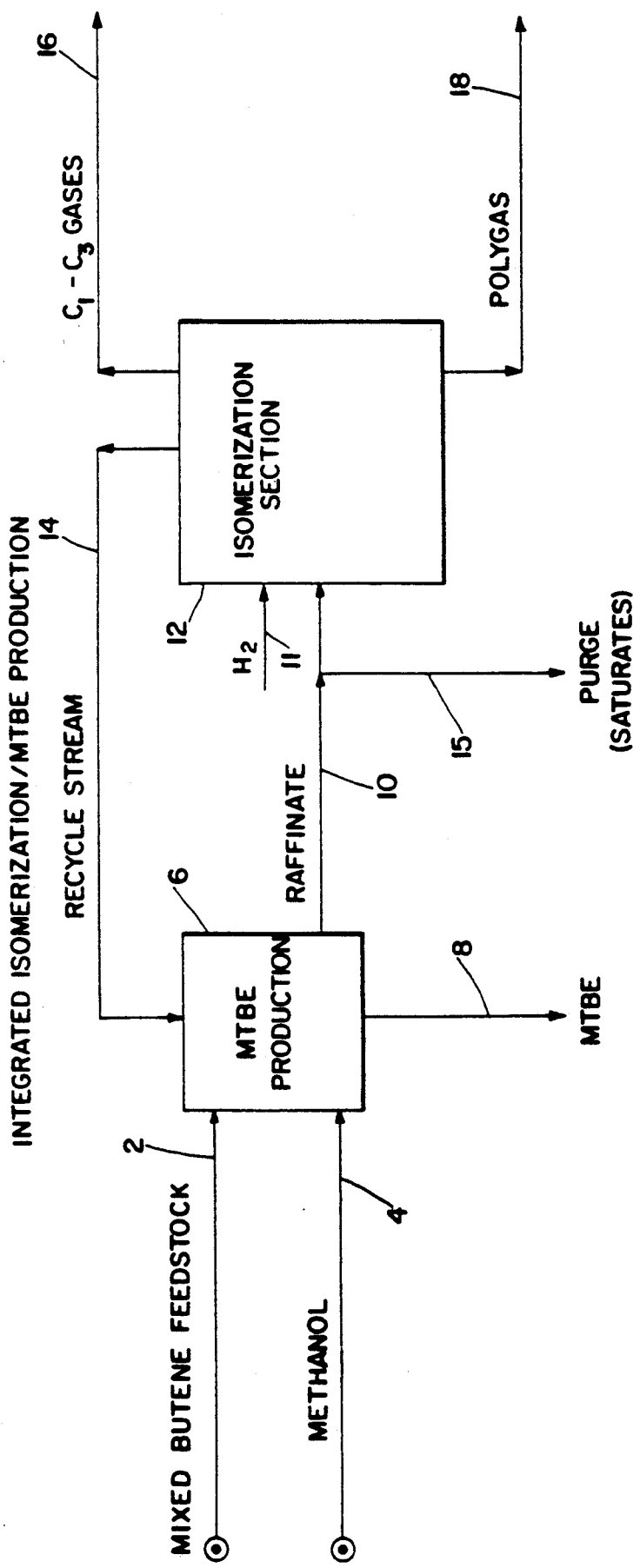
FIG. 1 is a schematic diagram for a process for the production of methyl tertiary-butyl ether (MTBE) which includes an isomerization section.

As discussed above, the olefin skeletal isomerization catalysts of the present invention employ materials comprising sulfated hydrous metal oxides which can be classified as solid acids, or solid super acids, the latter materials having acid strength or proton-donating ability at least as great as anhydrous (100 percent) sulfuric acid. The acidity of such solid acids is conveniently-measured in terms of the Hammett acidity function, $$H_o = pK_{BH+} - \log \frac{[BH^+]}{[B]},$$

where $K_{BH+}$ is the dissociation constant of the acid form of the indicator. $H_o$ can be visually determined by the use of a set of Hammett indicators, provided that the color of the unprotonated form is different from that of the conjugate acid (protonated) form.

An equivalent $H_R$ function, employing arylcarbinols as indicators, can be used. Arylcarbinols react with $H^+$ according to: $ROH + H^+ = R^+ + H_2O$
The $H_R$ function is defined by:

$$H_R = pK_{R+} - \log \frac{[C_{R+}]}{[C_{ROH}]}$$

The strength, nature and density of the acid sites produced can be critical in determining which types of reactions, if any, will be catalyzed by the materials produced. For example, catalysts for catalytic cracking generally require large numbers of strong acid sites so as to crack a variety of molecules, while skeletal isomerization is a more specific reaction requiring more subtle combinations of acid site strength and distribution.

For example, the minimum Bronsted acid strengths (and equivalents in H₂SO₄) required for various acid-catalyzed conversions of hydrocarbons are ranked in the table below with the arylcarbinol indicator values ($H_R$) and their equivalent Hammet ($H_o$) values taken from Peter A. Jacobs in *Characterization of Heterooenous Catalysts*, Marcel Dekker NY (1984), page 398.

Minimum Brönsted Acid Strength Required
For the Acid-Catalyzed Conversions of Hydrocarbons

| $H_R$ Required | $H_o$ | Reaction Type |
|---|---|---|
| < +0.8<br>~1.2 wt. % H₂SO₄ | 0 | Cis-trans Isomerization of Olefins |
| < −6.6<br>~48 wt % H₂SO₄ | −3.0 | Double-bond Migration |
| < −11.6<br>~68 wt % H₂SO₄ | −5.6 | Skeletal Isomerization |
| < −16.0<br>~88 wt % H₂SO₄ | −8.2 | Cracking of Alkanes |

The catalysts of the present invention require sufficient Bronsted acid strength to produce skeletal isomerization of olefins without substantial cracking of these or other hydrocarbon species. Substantial cracking would involve the cracking of at least about 20 to 35 volume percent of the olefin feedstock.

Catalyst acidity can also be determined by a thermometric titration of acid sites as performed on a Sanda 2000E instrument. The calcined catalyst to be titrated is suspended in 25 mL dry cyclohexane in an insulated container containing a magnetic spin bar. Metered amounts of a 2.5M solution of n-butylamine in cyclohexane are added and the temperature monitored. As the basic amine reacts with the acid sites on the solid, the temperature of the mixture rises. The end of the titration is determined as the time when the temperature no longer rises, i.e.. all acid sites have been neutralized. The number of acid sites per gram is related to the total volume of titrant required to reach the titration end (dV). The strength of the acid sites per meter squared of sulfated area is correlated with the temperature rise in the mixture during the titration (dT/SA).

Catalyst substrates which can be employed contain at least one hydrous metal oxide which can be converted to a solid acid by treatment with a sulfating agent. Such materials include alumina, silica-alumina, zirconia, iron oxides, titania, tin oxides, hafnium oxides and the like. In general, these hydrous metal oxides are formed from elements of Group(s) IVB, VIIIB, IIIA or IVA of the Periodic Table, but any suitable hydrous metal oxide which can be converted to a solid acid or have its inherent acidity modified by treatment with a sulfating agent can be employed.

The dried catalyst precursor comprising at least one hydrous metal oxide is treated with a suitable sulfating agent to form a solid acid, i.e., a material having a proton-denoting ability at least as great as that of a 68 weight percent aqueous solution of H₂SO₄. Such Bronsted acidity can conveniently be measured by the Hammett acidity function Ho, which should be numerically greater than approximately −5.6, preferably from about −5.6 to −8.2, and most preferably from about −5.6 to −7.5. For the preferred catalyst, results of thermometric titration have values from dT/SA of $3.0 \times 10^{-3}$ °C./m² or larger.

While not wishing to be bound by theory, it is believed that the formation of the solid acids having sufficient strength to catalyze skeletal isomerization in accordance with the present invention is due to the formation of Bronsted acid sites by the polar effects of the highly oxidized sulfate structures and the partial loss of waters of hydration from the hydrous metal oxide material. It appears that calcining both raises the oxidation state of the sulfur present and liberates water. See the discussion of Przystajko, et al., suora at page 271. See also Tanabe & Yamaguchi, suora for a partial discussion of these phenomena. The authors also report the development of "long lifetime superacid catalysts" for the other reactions including the skeletal isomerization of normal paraffins by incorporating a noble metal such as platinum in a sulfated zirconia catalyst. Surprisingly, the catalysts of the present invention which have been prepared for the skeletal isomerization of olefins by calcining a sulfated hydrous oxide such as alumina have been found to exhibit substantially stable activity without the addition of such noble metal components.

While not wishing to be bound by theory, it appears that catalysts with stable activity for skeletal isomerization of olefins are produced by modifying the surface of a hydrous metal oxide by the incorporation of sulfur oxides or sulfates to generate Bronsted acid sites of sufficient strength to bring about skeletal isomerization of olefins without catalyzing substantial cracking reactions. The surface modification should be carefully carried out so that the resulting acid sites have acid strength values that fall within a narrow distribution. While excessively high acid strength sites can cause cracking, sites with low acid strength can cause olefin polymerization. Thus acid sites whose strengths fall outside the preferred distribution of $-5.6 \leq H_o \leq -8.2$ can catalyze undesired side-reactions.

The alumina which can be used for the catalyst precursor of the present invention can be any suitable catalytic grade of crystalline alumina. Preferred aluminas are those which are active for converting olefins, including those forms of alumina known in the art as eta and gamma alumina. Preferred is the form of alumina known in the art as eta-alumina. Eta-alumina is conveniently produced by calcination of beta-alumina trihydrate. The most preferred is the form of alumina known in the art as gamma alumina, which can be produced by the calcination of boehmite (alpha alumina trihydrate) or pseudoboehmite. Gamma alumina is presently preferred over the eta form because it is easier to manufacture and generally offers better thermal stability. The alumina support should have a specific surface area of at least about 50 m²/g, preferably in the range of from about 50 to about 500 m²/g, and most preferably from about 100 to about 350 m²/g.

Other types of aluminas which can be used in the preparation of the sulfated aluminas of the present invention are those described as "substantially pure alumina" in co-assigned U.S. Pat. No. 4,139,491, which is incorporated herein by reference.

The alumina or other hydrous metal oxide materials need not necessarily be completely free of impurities. Thus, materials or substances other than $Al_2O_3$ and $SiO_2$, which cause little, if any, adverse effect upon the resultant catalyst's activity may be present. In other words, the catalyst precursor should consist essentially of hydrous oxides of the metals recited above. Impurities which are commonly associated with alumina and alumina-containing materials include for example, oxides of the alkali metals, the alkaline earth metals, and titanium of Group 4b of the Periodic Table of the Elements. In general, such impurities may be present in amounts not exceeding 5 wt. percent. However, it is preferred that the alumina or other precursor materials be substantially pure.

Included among these high purity aluminas are:
(i) alumina derived from chemically pure aluminum hydroxide which is obtained as by dehydration of the precipitate obtained by reaction of a soluble salt of aluminum (such as aluminum acetate) and a base (such as ammonium hydroxide);

(ii) alumina derived from chemically pure aluminum which is obtained by dissolving the aluminum in a solvent (e.g., caustic soda to form sodium aluminate) from which aluminum hydroxide is precipitated (e.g., by addition of acid), the hydroxide being dehydrated to alumina;

(iii) alumina derived by combustion of aluminum metal;

(iv) alumina found naturally occurring in pure state as a mineral;

(v) alumina recovered as a by-product from chemical reactions wherein, because of the nature of the reaction or the normal recovery technique, the alumina is recovered in substantially pure form; etc.

Typical of such pure aluminas is the pseudo-boehmite type of alumina derived as a by-product from the preparation of alcohols by a process which uses aluminum alcoholates. U.S. Pat. No. 2,892,858, for example, discloses a Ziegler synthesis of higher alcohols and the formation of such a by-product alumina. Such material is available commercially as "CATAPAL", a registered trademark for Conoco/Vista Chemical Co.

The pseudo-boehmite type alumina (which is typical of aluminas which may be used in practice of this invention) may typically contain impurities of $SiO_2$ at 60–120 ppm, say 80 ppm; iron oxides in amounts (as $Fe_2O_3$) of 27–61 ppm, say 50 ppm, and alkali metals in amounts (as $Na_2O$) of 15–70 ppm, say 40 ppm. The typical level of sulfur present as an impurity is less than 100 ppm. The alumina may be substantially free of other impurities.

This high-purity alumina, like other high purity aluminas which can be used in practice of the process of this invention, is particularly characterized by its initial substantial freedom from sulfate or similar anions; and sulfate, if present at all, is typically present in amounts less than about 1500 ppm, say 300–900 ppm or even less. In sulfating catalyst precursors such as alumina in the practice of this invention, there may be added to the alumina a catalytic amount of sulfate anion together with at least one catalytically acceptable cation. Although the sulfate anion may be added, for example, to an alpha alumina monohydrate pseudo-boehmite or to any of the aluminas to which it may be converted during processing, it is preferred to add the sulfate ion to the pseudo-boehmite derived gamma alumina.

A catalytic amount of sulfate ion is commonly about 0.5% to 50.0% of the precursor, more preferably 1.0% to 17.0%, say about 14.0 wt. % of the precursor. Since a typical catalyst contains other components (e.g., metals, oxides, etc.) this may correspond to about 0.4% to 40%, more preferably 0.5% to 13%, say about 12 wt. % of the total catalyst. Analytically this value is sometimes reported as "wt. % sulfur (determined as sulfate)"; this is an equivalent way of defining the catalytic amount of sulfate ion.

Amounts of sulfate ion in excess of the noted maximum tend to give decreased yields (due to cracking reactions) and shorter catalyst lifetimes, while amounts below the noted minimum tend to give both decreased yield and selectivity (due to polymerization reactions).

The sulfate ion is present together with a catalytically acceptable cation. Catalytically acceptable cations may include any cations which are found in sulfate compounds and which do not produce a detrimental or undesirable effect on the catalyst system. Catalytically acceptable cations may include those which appear to be inert, or those which moderate the catalytic activity, or those which possess desirable independent catalytic activity, or those which augment or promote the desired catalytic activity.

It will be apparent to those skilled in the art that the nature of the catalytically acceptable cations will be dependent on the ultimate catalytic process in which the catalyst is to be used. Common catalytically acceptable cations include (i) hydrogen (as in sulfuric acid); (ii) organic cations which are volatilizable or decomposable (as in alkyl sulfates such as methyl sulfate, ethyl sulfate, etc. or aryl sulfates such as benzyl sulfate); (iii) cations which are to be included in the final catalyst composition —e.g. aluminum; or if the final composition is to include, e.g., nickel, then the sulfate may be added as nickel sulfate subject to the maximum quantity of nickel which it may be desirable to have present in the catalytic composition. Thus, depending upon conditions, sulfates of metals such as manganese, zirconium, zinc, nickel, cobalt, copper, chromium, iron and vanadium can be used as sulfating agents.

The preferred cations are hydrogen or aluminum; and preferred compounds by which sulfate can be added include sulfuric acid, aluminum sulfate, and ammonium sulfate.

It is also possible within the scope of this invention to use sulfate precursors such as (a) bisulfates (typified by ammonium bisulfate); or (b) organic sulfonic acids typified by benzene sulfonic acid, toluene sulfonic acids, etc; or (c) sulfites (including ammonium sulfite) or (d) bisulfites (including ammonium bisulfite); or (f) persulfates (peroxysulfates, including persulfuric acids or fuming sulfuric acid) which under the conditions of oxidation prevailing may impart the desired properties to the alumina.

Sulfur trioxide is a preferred agent, because it is possible, for example, to introduce the desired sulfate ion (i) into an alpha alumina trihydrate before, during, or after its conversion to the alpha alumina monohydrate; (ii) into an alpha alumina monohydrate prior to, during, or after its conversion to gamma alumina; (iii) into a gamma alumina prior to, during or after further treatment; etc.

Sulfur trioxide ($SO_3$) is an essential component in preparing certain catalyst compositions of the present invention. It is added to the hydrous metal oxide precursor in a catalytically effective amount. It may be charged directly as sulfur trioxide in the vapor or gaseous phase. Alternatively, it may be provided indirectly by charging to the hydrous metal oxide a mixture of sulfur dioxide ($SO_2$) and nitrogen dioxide ($NO_2$) which reacts to produce sulfur trioxide and inert (for purposes of the present invention) nitric oxide (NO). When a mixture of sulfur dioxide and nitrogen dioxide is employed, a stoichiometric mole ratio of at least 1:1 is required. It is preferred, however, to employ an excess of sulfur dioxide, usually on the order of about 2 to 3 moles per mole of nitrogen dioxide.

In general, when providing the sulfur trioxide, the indirect method of charging a mixture of sulfur dioxide and nitrogen dioxide to the hydrous metal oxide material is preferred in that both sulfur dioxide and nitrogen dioxide, as well as nitric oxide, exist in the gaseous state at ambient temperatures (approximately 25° C.) and above while sulfur trioxide exists as a liquid at ambient temperatures and under the usual and preferred preparative conditions would first have to be converted to a vapor prior to contacting the hydrous metal oxide.

As previously indicated, the catalyst compositions of the present invention are sulfated, and for certain embodiments, an essential component is sulfur trioxide. It is recognized, of course, that when a mixture of sulfur dioxide and nitrogen dioxide is charged to the reactor to provide the sulfur trioxide, the absorbed species may in fact be a complex or combination of sulfur trioxide and nitrogen dioxide. However, regardless of the actual composition of the absorbed species, it is conveniently referred to herein as sulfur trioxide and is meant to encompass all such compositions, whether sulfur trioxide, sulfur trioxide-nitrogen dioxide complex, or some combination thereof, as well as unreacted mixtures of sulfur dioxide and nitrogen dioxide.

The catalyst composition of the present invention are normally prepared by contacting the hydrous metal oxide precursor with sulfur trioxide (directly or indirectly as previously described) in the vapor phase under conditions conducive to the formation of the sulfated material and for a time sufficient to induce the desired weight gain. The amount of added sulfur trioxide (as indicated by the gain in weight) is not narrowly critical. All that is necessary is that a catalytically effective amount of sulfur trioxide be added. In general, it has been found that at least 1 weight percent, based on the weight of the catalyst composition, of sulfur trioxide is required to provide the enhanced activity and stability exhibited by the catalyst compositions of the present invention. Also, although not critical, an upper limit of about 40 weight percent, with about 12 weight percent being preferred, has been found to be desirable in that little, if any, advantage is demonstrated for higher concentrations of sulfur trioxide. Thus, both higher and lower concentrations than the stated 1 to 40 weight percent range can be employed, if desired, but since such concentrations offer no particular advantage over the stated desirable range, and may in fact affect adversely the catalyst activity, particularly at concentrations less than about 1 weight percent, the stated 1 to 40 weight percent range is desirably employed.

The vapor-phase conditions under which the catalyst compositions are prepared can vary widely. All that is necessary is that the sulfur trioxide, whether charged directly or indirectly, exist in the vapor phase while contacting the hydrous metal oxide. Thus, the catalyst preparation can be conducted at temperatures ranging from ambient temperatures (about 25° C.) (when sulfur dioxide and nitrogen dioxide are employed to provide the sulfur trioxide) to about 300° C. or higher. Preferred temperatures, however, range from about 150° C. to about 250° C., with 175° C. to about 225° C. being particularly preferred. At such preferred temperatures, the uptake of sulfur trioxide is reasonably rapid with a minimum of loss of reactant gases resulting from unreacted pass-through. In general, and for convenience, the catalyst preparations can be performed at the temperature to be employed in the subsequent reaction in which the catalyst is to be employed.

Such catalyst preparations are conducted under substantially anhydrous conditions. This is necessary since sulfur trioxide readily undergoes reaction with water to form sulfuric acid which, prior to formation of the adducts comprising the catalyst compositions of the present invention, may exhibit an adverse effect in subsequent reactions. As employed herein, the term "substantially anhydrous" means no more than 5 wt. percent water is present in the reaction as part of the catalyst-forming components.

The catalyst compositions of the present invention are conveniently prepared in an apparatus of the type suitable for carrying out chemical reactions in the vapor phase. In this manner the catalyst preparation can be performed in the same reactor as that to be employed for the subsequent isomerization reaction. It can be conducted in a fixed bed, moving bed, or a fluidized bed system to effect contacting of the hydrous metal oxide precursor and the sulfur trioxide. As previously noted, catalyst preparation is preferably carried out by continually passing a vaporous mixture of the sulfur dioxide and nitrogen dioxide in a 2-3/1 mole ratio over a bed of the hydrous metal oxide under substantially anhydrous conditions at a temperature from about 25° C. to about 300° C., and usually, about 175° C. to about 225° C.

Specifically it is possible to introduce sulfate ion (i) after the final hydrous metal oxide composition such as alumina is formulated; or, (ii) before or after any of the drying or calcination steps.

It is, however, preferred that the catalytic amount of sulfate ion and catalytically acceptable cation be added to the gamma alumina or other hydrous metal oxide prior to calcining. Preferably the so-obtained gamma alumina contains a catalytic amount of sulfate ion distributed over the exposed outer surface of the alumina.

As mentioned above, various aqueous sulfate ion compositions can be used as sulfating agents. Preferred of these sulfate ion compositions are sulfuric acid, ammonium sulfate and aluminum sulfate, each of which produce catalysts of differing activity and stability. Sulfuric acid is presently most preferred for treating aluminas.

It will be apparent that the preferred catalytically acceptable cation be one having a soluble sulfate. Group IA and IIA metals such as sodium, potassium, magnesium and calcium, when present as their sulfates, tend to produce catalysts that give somewhat lower conversion with lower yield of desired iso-olefin product and they also tend to give increased concentrations of undesired by-products.

In the practice of the preferred embodiment, 100 parts of e.g. gamma alumina or other hydrous metal oxide may be immersed in 10 to 1000 parts, say 60 to 175 parts of aqueous solution containing 0.50 to 100 parts, say 14 parts of sulfate ion. This may correspond, for example, to 0.51 to 102 parts, say 14.3 parts of sulfuric acid; or to 0.59 to 119 parts, say 16.6 parts of aluminum sulfate $Al_2(SO_4)_3$; etc.

The gamma alumina is allowed to remain in contact with the aqueous solution at 10° C. to 100° C., say 25° C. for 0.25 to 24 hours, say 1 hour. If desired, impregnation may be effected by use of a portion of the aqueous solution which is allowed to contact the alumina for 0.25 to 24 hours, say 1 hour. This portion of solution may then be poured off and replaced by a second portion which is allowed to contact the alumina for 0.25 to 24 hours, say 1 hour.

The alumina, now bearing the catalytic amount of sulfate ion distributed over the outside of the alumina and throughout substantially the entire body of alumina is then dried at 80° C. to 260° C., say 150° C. for 0.27 to 24 hours, say 1 hour. The so-dried alumina is preferably then calcined at 370° C. to 760° C., say 550° C. for 0.24 to 24 hours, say 2 hours. The alumina so prepared may be found to contain 1 weight percent to 17 weight percent, say 14.0 weight percent of sulfate ion.

The so-prepared alumina may be a novel gamma alumina containing a catalytic amount (typically 0.5 weight percent to 50.0 weight percent, preferably 1.0 to 17.0 weight percent, say 14.0 weight percent) of sulfate anion distributed over the outside of said gamma alumina and throughout substantially the entire body of said gamma alumina—together with at least one catalytically acceptable cation.

Specific immersion techniques, referred to as equilibrium adsorption, are described by Brunelle in "Preparation of Catalysts by Metallic Complex Adsorption on Mineral Oxides", *Pure & Applied Chem.*, Vol. 50, pp 1211-1229 (1978); by Wang and Hall in "The Preparation and Genesis of Molybdena-Alumina and Related Catalyst Systems", *Journal of Catalysis*, Vol. 77, pp. 232-241 (1982) and D'Aniello, in "Anion Adsorption on Alumina", *Journal of Catalysis*, Vol 69, pp. 6-17 (1981). All of these publications are incorporated herein by reference.

It will be apparent to those skilled in the art that when the sulfate is added in the form of sulfuric acid, the catalytically acceptable cation may be considered to be hydrogen. In this instance, it is probable that the sulfuric acid may react with a portion of the alumina to form aluminum sulfate and water, which latter may be expelled during calcinations; and thus the catalytically acceptable cation may alternatively be considered to be aluminum. Similar considerations may prevail when the sulfate is added as ammonium sulfate, methyl sulfate, etc., wherein the ammonium or methyl, etc. cations may be volatized etc. under conditions of calcining to leave aluminum as the net catalytically acceptable cation.

The sulfate content of the alumina, or the alumina-derived catalyst, may be added to the high purity (e.g., sulfate-free) aluminas ab initio or at any desired stage during processing. For example, the sulfate content could be added at any stage in the interconversion of alpha monohydrate, alpha trihydrate, or beta trihydrate to gamma or eta alumina. It may be added during further treating, i.e. before or during or as an integral step in addition of other components—e.g., as by addition of nickel sulfate, etc.

In the preferred embodiment, the catalyst composition may be in the form of pellets, cylinders, or randomly shaped particles; a typical catalyst composition may be in the form of cylinders.

Silica-alumina materials which can be used for the catalyst precursor can be prepared in the same manner as amorphous silica-alumina catalysts, e.g., by producing silica-alumina slurry, spray drying, washing the product and drying. Optionally, a clay diluent can be present in the silica-alumina slurry. Such slurries can be prepared by admixing colloidal alumina (boehmite) and colloidal silica, allowing the catalyst precursor properties to vary over a wide range from catalytically inert to active. The activity, thermal stability, surface area and pore distribution of the material can be controlled by varying the amounts and particle size distributions of the respective colloids.

The catalyst precursor can also contain a porous clay material which has suitable binding properties and is resistant to the temperature and other conditions employed in the process. Naturally occurring clays can be used in the raw state as originally mined or initially subjected to calcination, acid treatment, chemical modification or purification.

Examples of suitable clays which can be used include the bentonite and kaolin families. Bentonites are mixtures of clays, mainly montmorillonites, which may also contain kaolinite clays. The Wyoming bentonites and montmorillonites are preferred because of their relatively high purity. Kaolin clays include, for example, the Dixie McNamee-Georgia and Florida clays and others in which the main mineral constituent is halloysite, kaolinite, dickite, nacrite or anauxite. Other clays may also be found to be suitable for use in the present process.

The catalysts of the invention are prepared by drying the catalyst precursor by any suitable method, treating the precursor with a suitable sulfating agent, drying the sulfate-treated precursor, and subsequently calcining to activate the sulfated metal oxides and produce a finished catalyst.

The sulfated catalyst precursors can be dried in air under temperature and time conditions to reduce the overall moisture content to less than about 5 weight percent. This drying step preferably is conducted at temperatures in the range of from about 90° C. to about 260° C., for suitable periods of time to attain the desired level of moisture content.

The dried impregnated catalyst precursor material is calcined at a suitable temperature and for a time effective to produce an activated catalyst which is effective in converting normal olefins to branched species under isomerizing conditions (without substantial cracking) and displays substantially stable activity in such reactions. By "substantially stable activity" it is meant that the rate of loss in catalyst activity with time should be no greater than that observed for the untreated (i.e., unsulfated) hydrous metal oxide. The temperature should be at least about 300° C., preferably ranging from about 375° C. to about 750° C., most preferably from about 450° C. to about 550° C. With at least some hydrous metal oxides, calcining at temperatures ranging from about 300° C. to about 600° C. are preferred, since calcining temperatures above about 600° C. may cause superacidity sites to be generated. The calcining time can range from about 0.5 hour to about 8 hours and preferably ranges from about 0.5 to about 2 hours. Calcining can take place in an atmosphere of an oxygen-containing gas. The oxygen content can range from as little as about 2 volume percent in mixtures of inert industrial gases to substantially pure oxygen. It is presently preferred to use air in a flowing current to remove impurities as the calcining proceeds. The gas pressure during calcining can range from subatmospheric to slightly elevated pressures, but is preferably about atmospheric pressure.

The skeletal isomerization process of this invention is carried out by contacting the feed with the catalyst, using any suitable contacting techniques, at temperatures at which skeletal isomerization of the feed olefins occurs. The feed is preferably maintained in the vapor phase during contacting. The temperature is preferably in the range of about 300° to about 500° C., more preferably about 350° to about 475° C. The weight hourly space velocity (WHSV) based upon the olefin content is not narrowly critical but will generally be within the range of about 0.1 to about 320 hour , preferably from about 0.1 to about 20 hour$^-$. Ranges of suitable process temperatures and the corresponding WHSV (olefin) values are shown below in tabular format.

| T (°C.) | 300–350 | 350–500 | 350–450 | 400–500 |
|---|---|---|---|---|
| WHSV (olefin) | 0.1–20 | 0.1–320 | 0.1–250 | 0.1–250 |

At the lower temperatures, the side products are mainly polygas; the temperatures near 500° C. minimize polygas production, but cracking begins to take place.

Any convenient partial pressure of feedstock can be used, with the lowest practical pressure normally preferred in order to minimize side reactions such as polymerization. Preferred olefin partial pressures are within the range of about 0.3 to about 40 psig, more preferably about 1 to about 3 psig. The process is preferably carried out in the presence of hydrogen at a partial pressure in the range of from about 0.1 to about 20 psig, preferably from about 0.3 to about 16 psig.

The isomerization feedstock contains at least one alkene, preferably an alkene having from 4 to about 12 carbon atoms per molecule, more preferably an alkene having from 4 to 6 carbon atoms per molecule. Alkenes having 7 or more carbon atoms are generally more likely to crack into light gases than to undergo skeletal isomerization. The alkene may have terminal or internal double bonds. Normal alkenes, especially normal butenes, are preferred feedstocks. Butene feedstocks may contain 1-butene, 2-butene or mixtures thereof. Examples of other normal alkenes which are useful feedstocks are 1- and 2-pentenes; 1-, 2- and 3-hexenes; 1-, 2-, and 3-heptenes; and 1-, 2-, 3-, and 4-octenes. The normal alkenes can be accompanied by other hydrocarbons, typically other hydrocarbons having the same numbers of carbon atoms as the alkene feed. In the case of normal butenes, examples of other hydrocarbons are normal butane and isobutane.

Particular feedstocks contemplated for use in the present process are fractions containing n-butenes, optionally mixed with isobutene, isobutane and n-butane. Such fractions are commonly produced in petrochemical plants and refineries as, for example, after the separation of 1,3-butadiene butadiene from a C$_4$ cut or in the cracking of waxy distillates. Isobutene present in such fractions is commonly converted by catalytic reaction with methanol to produce methyl tertiary-butyl ether ("MTBE"). MTBE is separated by distillation, leaving a residual C$_4$ cut. In an alternative process, isobutene present in such fractions may be oligomerized to produce oligomers which are then separated, again leaving a residual C$_4$ cut. In either MTBE production or oligomerization, a mixture of n-butenes, n-butane and isobutane remains in the residual material. It is desirable to produce additional isobutene from the residual material and return the isobutene for further conversion by the reactions mentioned above.

The olefinic feed stream can contain inert gaseous diluents (e.g. paraffins, N$_2$, steam, etc.). The diluent be present in any desired proportion, e.g., up to about 80 weight percent of the olefinic feed stream. Hydrogen can be present in the feed stream in addition to such diluents, but preferably is present only when a hydrogenation catalyst is employed.

Selection of isomerization conditions is dependent on the olefins to be isomerized. In general, lower temperatures are used for feeds containing larger olefin molecules. Depending on the specific skeletal isomerization catalysts chosen to carry out the steps of the invention, any suitable reaction technique can be utilized, such as fixed bed reaction, fluidized bed reaction, liquid phase batch and continuous operations, and the like. Conventional methods can be used to separate the materials present in the reaction effluent, including fractionation, adsorption, and the like. Fractionation is generally preferred. Saturated materials which accumulate in the system can easily be removed by suitable techniques well known in the art.

In the process according to the invention, the conversion of n-alkenes into isoalkenes, preferably n-butenes into isobutene, almost up to the establishment of thermodynamic equilibrium is achieved. This equilibrium, between 350° to 500° C., provides about 34 to 41 percent by weight isobutylene in the case in which the n-butenes are allowed to isomerize to all possible C. isomers and hydrogen. This equilibrium is frequently not achieved in the case of a single contact of the mixture to be employed according to the invention with the catalyst to be employed during the invention. However, in a particular variant of the process, the product stream leaving the catalyst bed can be divided up, and only one part is directly conveyed to the working-up process, while the other part is again conducted over the catalyst bed. This division of the product stream for recycling can vary within wide limits, for example between the proportions 1:9 to 9:1 of worked-up or recycled material. In this process, a high recycling rate implies a smaller throughput, relative to a constant catalyst charge and constant remaining reaction conditions, but brings a desired shift of the spectrum of components in favor of the isoalkene, e.g. of the isobutene, almost to the thermodynamic equilibrium. On the other hand, a lower recycling rate implies a higher throughput but a poorer approach to the thermodynamic equilibrium. A decision concerning the amount of the recycling rate depends, other process parameters being constant, above all on the composition of the starting hydrocarbon mixture which is available. However, with the catalysts according to the invention, the process can, in general, be operated without a high recycling rate. This can be optimized by simple preliminary experiments.

Referring to FIG. 1, a preferred embodiment of the invention is directed to an integrated process for skeletal isomerization of normal butenes and the production of methyl tertiary-butyl ether (MTBE). Streams of a mixed butene feedstock (2) and methanol (4) are reacted in an MTBE synthesis reactor (6), the methanol reacting with the isobutene in the mixed feedstock to form MTBE which is taken off via line 8. The MTBE synthesis reactor acts as a $C_4$ separation unit, since the methanol reacts selectively with isobutene. Other mixed olefin streams could be treated in the same manner, e.g. reacting methanol with isoamylenes to form tertiary-amyl methyl ether (TAME). Other alcohol streams could be employed in a similar manner; e.g., reacting ethanol with mixed butenes to form ethyl tertiary-butyl ether (ETBE). The alcohol stream can contain at least one alkanol having from 1 to about 5 carbon atoms. Depending upon whether streams containing substantially single alcohols or mixtures thereof are employed, the corresponding alkyl tertiary-alkyl ether or mixtures containing various groups can be produced. The product raffinate stream (10) is fed to the skeletal isomerization unit (12) wherein a catalyst of the present invention is employed to isomerize normal butenes to isobutene for recycle to the MTBE via recycle line (14). Hydrogen can optionally be introduced to the skeletal isomerization unit at (11). Saturated species can be separated and purged from the raffinate via line 15, or as part of the by-products ($C_1$-$C_3$ gases and polygas) which are separated from the isomerization section via lines 16 and 18. Such an integrated process permits a mixed feed stream of butenes (or other alkenes) to be used most effectively in the production of MTBE (or other alkyl tertiary-alkyl ethers) via the skeletal isomerization of normal alkenes and recycle to the MTBE reactor. Alternatively, the product stream (14) from the skeletal isomerization unit can be sent to a second MTBE reactor for non-integrated operations. The skeletal isomerization processes and catalysts of the present invention are of course useful in processing normal alkene-containing feed streams from a variety of sources, including, e.g., a dehydrogenation process.

Typically, prior art processes for the skeletal isomerization of olefins have required contacting the feedstock at elevated temperatures with strongly acidic catalysts. Most of the metal oxide catalysts employed required treatment with halides to produce the required acidity, often requiring halide treatment during the reaction as well. Such halided catalysts involve significant corrosion problems as well as increased processing expenses, since measured amounts of halides may need to be continually added with the feed. Furthermore, water and/or methanol must be rigorously excluded from the feeds contacting such catalysts, since their presence would deactivate the halided catalysts.

As will be seen in the examples below, catalysts of the present invention based upon sulfated alumina have been found to exhibit excellent activity in converting n-butenes to isobutene. The results of these examples may be compared with the work of Choudhary and Doraiswamy (referred to in Choudhary, 1974, supra, p. 37) in which 46 solid catalysts were tested for the conversion of n-butene to isobutene at 400 C, atmospheric pressure and W/F =40. The best catalyst, fluorinated alumina containing 1 weight percent F., provided 33.5 percent conversion, 87.1 percent selectivity for isobutene and a half life of 62.5 hours. The use of the catalysts of the present invention of course eliminates the disadvantages associated with halided catalysts. In addition to the disadvantages discussed above of the constant addition of halide to the feedstock, this technique of counteracting impurities in the feed which would poison the prior art halided catalyst may be ineffective when the catalyst deactivation is due to the formation of polymer and/or coke on the catalyst surface.

For catalysts exhibiting a decline in activity due to a build up of polymeric materials on the surface of the catalyst, a simple solvent wash pumped through the catalyst bed should restore most of the original activity. Spent catalysts can be regenerated by heating in a similar oxygen-containing gas, such as air, at temperatures ranging from about 200° C. to about 700° C. and resulfating the catalyst material when necessary. Such recalcining and resulfating can be done on a continuous basis with various moving-bed catalyst systems, and fixed catalyst beds can be regenerated while an alternate unit is in service.

EXAMPLES

The invention is further illustrated by reference to the following non-limiting examples.

EXAMPLE I

To 25.4 g of gamma-alumina was added dropwise a solution of 2.67 g concentrated sulfuric acid in 22.7 g deionized water. The impregnated catalyst was dried overnight at 120° C. Analysis of this material showed it to contain 2.95 wt. percent sulfur. Five grams of the catalyst was loaded into the reactor and calcined/activated in situ at 550° C. for three hours in flowing air. The catalyst was evaluated at 425° C., 1 atm pressure and a WHSV of 2.0 hr$^{-1}$, with the feed to the reactor being composed of 30 wt. percent 1-butene and 70 percent n-butane.

Figure 2:
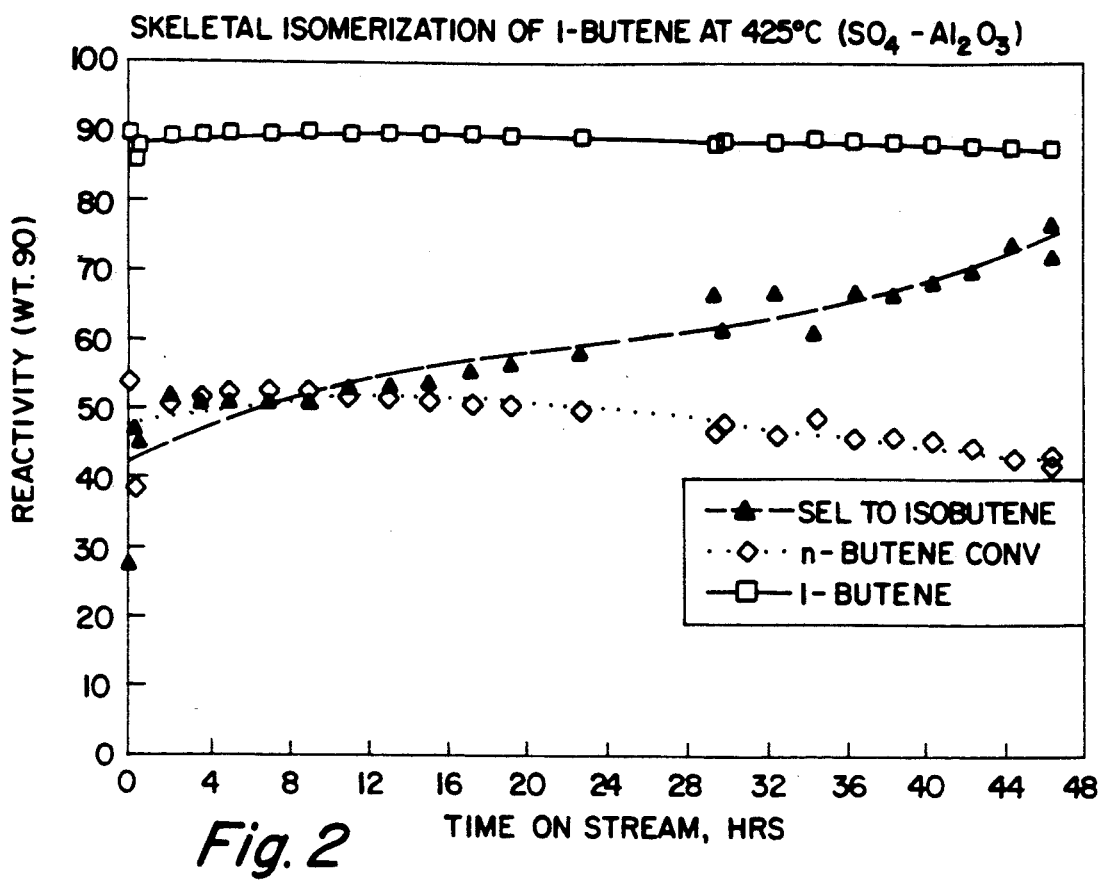
FIG. 2 is a plot of Reactivity versus Time on Stream for the isomerization of 1-butene with a sulfated alumina catalyst of the invention.
Figure 3:
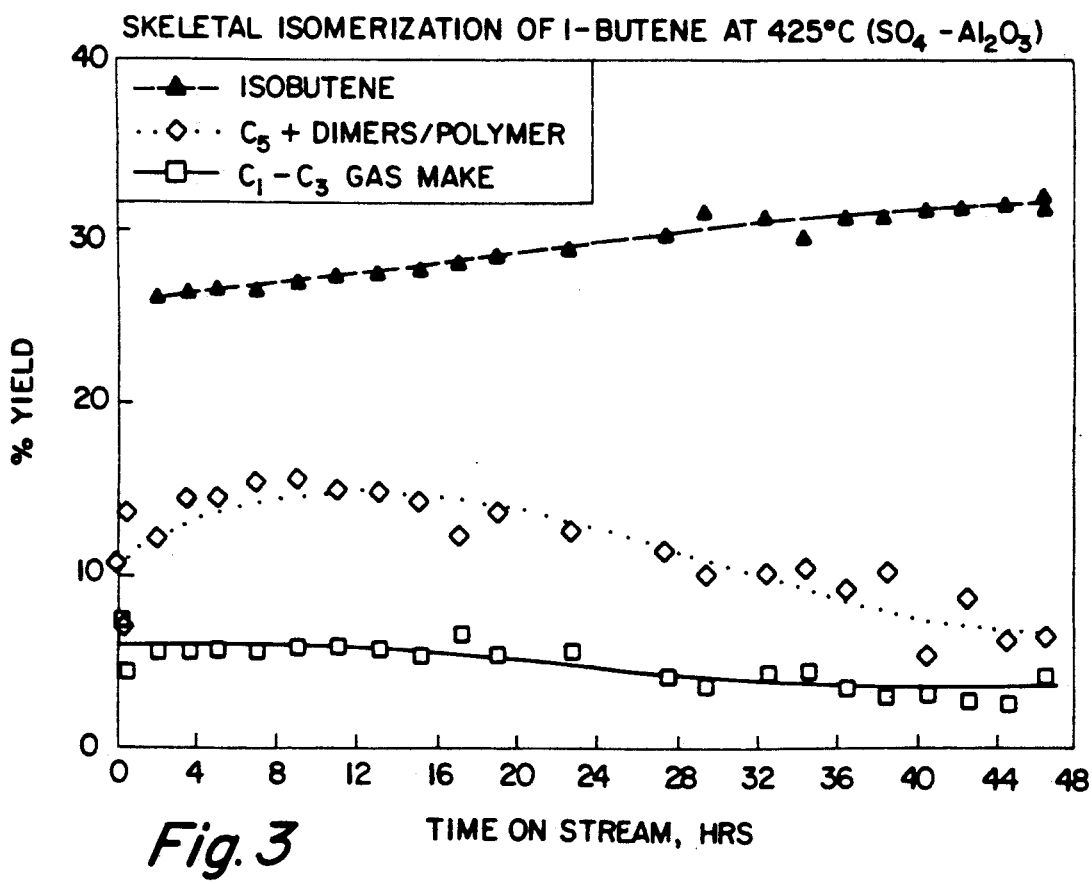
FIG. 3 is a plot of Percent Yield versus Time on Stream for the isomerization of 1-butene with a sulfated alumina catalyst of the invention.

As shown in FIG. 2, n-butene conversion is 42 wt. percent at the end of 45 hours-on-stream. As shown in FIG. 3, the yield of isobutene actually increases during the run while the yield of $C_5+$ oligomer decreases. Thus, selectivity to isobutene after 45 hours on-stream is a very respectable 75 percent which is equivalent to that of a chlorided alumina as reported in U.S. Pat. No. 4,654,463. This example does not represent optimized processing conditions, but based upon reports in the literature with chlorided aluminas, it is expected that maximum selectivity to isobutene would be obtained at butene conversion levels of 41 percent and lower. Thus, optimum selectivity to isobutene should be realized by adjusting the reaction temperature, flow rates and possibly the sulfate content of the alumina or other support.

COMPARATIVE EXAMPLE A

Luy, et al. reported in *React. Kinet. Catal. Lett.*, supra, that sulfating enhanced the activity of zirconia/alumina in the skeletal isomerization of 1-butene. Although the use of pure alumina produced only n-butenes in equilibrium conditions, the addition of sulfate ion to this alumina reportedly made it possible to obtain significant amounts of the skeletal isomer. However, such skeletal isomerization was deactivated during the first 90 minutes of the run.

As reported in the article, catalysts were prepared by impregnations of a $\gamma$-$al_2O_3$ (DK-300 from Cyanamid Ketjen, Sg=200 m$^2$ g$^{-1}$) with 1.4 cm$^3$ of an aqueous solution of zirconyl chloride per gram of $Al_2O_3$ at room temperature over 6 h. After impregnations, samples were repeatedly washed with a 3.3 M NH$_4$OH solution in order to eliminate remaining Cl$^-$. Then sulfate ion was introduced by pouring 15 cm$^3$ of 1 N H$_2$SO$_4$ per gram of oxide on a filter paper. After drying, samples were calcined in air at 620° C for 6 h, and then kept in an inert atmosphere (He) until being used. Pure $Al_2O_3$, sulfated $Al_2O_3$ and sulfated $Al_2O_3$ treated as $ZrO_2$ containing catalysts, were also tested. As indicated in Luy's Table 1, the sulfated alumina catalyst had a BET specific surface area of 184 m$^2$/,g (compared to 200 for pure alumina) and contained 8.0 wt. percent sulfate ion.

Isomerization of 1-butene was reportedly carried out in a continuous plug-flow system (1 atm, isothermal), using the necessary mass for each catalyst in order to obtain the same surface area into the reactor (75 m$^2$), and flow rates of 1-butene (Matheson 99.5 percent ) of 12 cm$^3$ min$^{-1}$, and carrier gas (N$_2$) of 62 cm$^3$min$^{-1}$. Catalysts were activated at 500° C for 2 h. in air flow, and then the temperature was decreased until reaching reaction conditions (573° K.). Reaction products were analyzed chromatographically on line by using a 6 m long, ⅛ in O.D. column of 25 percent dismethylsulfolane on Chromosorb P and a Flame Ionization Detector.

The operating conditions and results for Luy's work (Comparative Example A) and Example I of the present invention are summarized in the Table below.

TABLE

| | Example | |
| --- | --- | --- |
| | A | I |
| Pressure: | 1 atm | 1 atm |
| WHSV: | 4.85 | 0.6 based on butene only |
| Feed (wt. %) | 16 butene: | 30 butene: |
| | 84 nitrogen | 70 butane |
| Temp: | 300° C. | 425° C. |
| Isobutene Yield (%) | 7.8 dropping to 3.2 within 90 min. | 26–32 |
| Concentration of Isobutylene in Product | 1.25% | 7.8–9.6% |

It is apparent that in Luy's process the catalyst lost 59 percent of its activity within 90 minutes. Surprisingly, much higher levels of activity for isobutene production were obtained in our Example I, and such activity was maintained over 48 hours of run time.

EXAMPLE II

A second sample of catalyst was prepared as outlined in EXAMPLE I by impregnating 96.69 g gamma-alumina with a solution of 9.706 g concentrated sulfuric acid dissolved in 86.96 g deionized water. The impregnated catalyst was dried overnight at 120° C. analysis of this material showed it to contain 3.29 wt percent sulfur. This is presently considered the best mode of the invention. 0.81 grams of the catalyst was loaded into the reactor and calcined/activated in situe at 550° C. for three hours in flowing air. The catalyst was evaluated at 425° C., 1 atm pressure and a WHSV of 123 hour$^-$with the feed to the reactor being composed of 39.5 wt. percent 1-butene and 60.5 percent n-butane.

EXAMPLE III

Another catalyst was prepared and evaluated as described in EXAMPLE II but using 20.88 g aluminum sulfate hydrate in place of the sulfuric acid. Analysis of the dried catalyst showed it to contain 3.14 wt percent sulfur.

EXAMPLE IV

A similar catalyst was prepared and evaluated as described in EXAMPLE II but using 12.419 g ammonium sulfate in place of the sulfuric acid. The dried catalysts contained 3.27 wt percent sulfur.

EXAMPLE V

Using the same gamma-alumina support that was employed in EXAMPLE II, Luy's procedure as described in COMPARATIVE EXAMPLE A was followed to prepare and activate a sulfated alumina catalyst. Analysis of the dried catalyst showed it to contain 3.46 wt percent sulfur as compared to 2.67 wt percent of Luy's catalyst. The surface areas of the two catalysts at 182 and 184 m,/gm can be considered to be equivalent.

EXAMPLE VI

The same gamma alumina support of EXAMPLE II was immersed in a 1.0 molar solution of sulfuric acid (pH of the solution is approximately 0.6) overnight. Excess solution was removed by decanting and the treated alumina was collected by vacuum filtration. Analysis of the dried material showed it to contain 4.68 wt percent sulfur.

Figure 4:
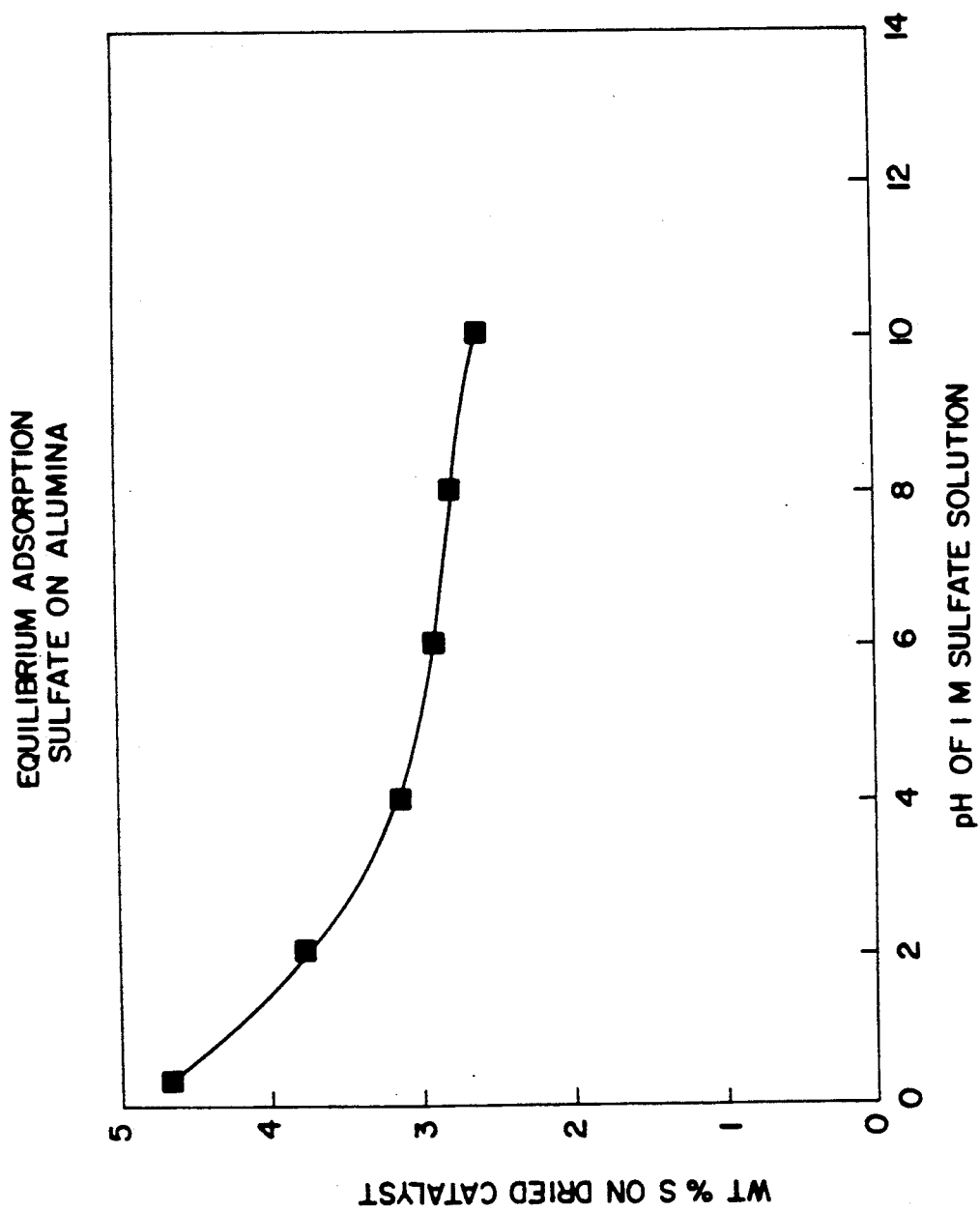
FIG. 4 is a plot of the sulfur loading of sulfated gamma alumina supports versus the pH of the sulfating solution employed.

The sulfur loading of a hydrous metal oxide can vary as a function of the pH of the sulfate solution into which the hydrous metal oxide is immersed. FIG. 4 shows the sulfur loading of gamma alumina to decrease from 4.68 to 2.60 wt percent as the pH of a 1.0 molar sulfate solution is varied from a pH of 0.6 to a pH of 10.0 by the addition of a concentrated solution of ammonium hydroxide to a solution of sulfuric acid. Catalysts prepared by the immersion (or equilibrium adsorption) technique exhibit an even adsorption of the colored Hammet indicators, suggestive of a more even distribution of new acid sites.

Some of the catalysts prepared by the immersion technique are also found to exhibit a loss as measured by TGA of 7 to 10 percent of their weight when heated at temperatures above 600° C. This high temperature weight loss may be associated with the loss of the desired Bronsted acid sites, possibly due to their transformation into Lewis acid sites. Thus the high temperature calcination/activation of Luy's procedure would alter the nature of the catalyst surface and may explain the low reactivity and life of the catalyst of Example V and Luy's reported results. (This observation may also suggest that some small amount of steam may be beneficial if added during catalyst regeneration.)

EXAMPLE VII

| Catalyst | BET S.A. | % S | Thermometric Titration | |
|---|---|---|---|---|
| | | | dV (ml/gm) | dT/SA ($\times 10^3$) |
| II | 211 | 3.29 | 2.57 | 4.52 |
| III | 230 | 3.14 | 2.85 | 3.56 |
| IV | 224 | 3.27 | 2.42 | 3.52 |
| V | 182 | 3.46 | | |
| VI | 188 | 4.68 | | |
| $Al_2O_3$ | 244 | | 1.18 | 1.53 |
| $SiO_2$—$Al_2O_3$ | 397 | | 1.80 | 2.45 |

EXAMPLE VIII

| | Results of Thermogravimetric Analysis Temperature in °C. and (Percent wt Loss) | |
|---|---|---|
| Catalyst | | |
| II | 132 (1.15%) | 319 (3.36%) |
| III | 139 (1.41%) | 347 (3.13%) |
| IV | 133 (0.84%) | 324 (3.31%) |
| V | 655 (7.64%) | |
| VI | 357 (3.60%) | 606 (10.3%) |

EXAMPLE IX

| Catalyst | % n-Butene Converted at | | | |
|---|---|---|---|---|
| | 0.5 | 2.0 | 4.0 | 12 hrs |
| II | 63 | 63 | 59 | 47 |
| III | 62 | 62 | 58 | 40 |
| IV | 23 | 36 | 43 | 43 |
| V | 64 | 55 | 49 | N.A. |
| VI | 69 | 69 | 66 | 51 |
| $Al_2O_3$ | 44 | 48 | 48 | 49 |

These data illustrate that the sulfated alumina catalysts of the present invention provide a highly desirable combination of high activity for isobutene production and catalyst stability.

HYPOTHETICAL EXAMPLE

Separate catalysts containing sulfated hydrous oxides of tin, titanium and zirconium are prepared by drying and calcining/activating as described above in Example I. Testing of the catalysts for the skeletal isomerization of olefins as described in Example I above produces performance which is at least equivalent to that of Example I.

While the processes and catalysts of the invention have been particularly illustrated by examples of the skeletal isomerization of n-butenes, they are equally applicable to similar isomerizations of the higher n-olefins such as n-pentenes, n-hexenes, n-heptenes and the like. Reasonable variations and modifications are possible within the scope of the disclosure without departing from the spirit or scope of the invention, which is defined solely by the appended claims.

We claim:
1. A catalyst composition for the skeletal isomerization of normal olefins prepared by a process comprising the steps of:
   (a) treating a dried catalyst precursor comprising at least one crystalline zirconia with a sulfating agent comprising zirconium sulfate to deposit sufficient suflate species to catalyze the skeletal isomerization of said normal olefins under isomerizing conditions without substantail cracking;
   (b) drying the resulting sulfated catalyst precursor; and
   (c) calcining the dried sulfated precursor to produce an activated catalyst comprising a solid acid.

* * * * *